United States Patent
Speier et al.

(10) Patent No.: US 7,558,615 B2
(45) Date of Patent: Jul. 7, 2009

(54) METHOD AND APPARATUS FOR INTERVENTION IMAGING IN MAGNETIC RESONANCE TOMOGRAPHY

(75) Inventors: Peter Speier, Erlangen (DE); Frank Wacker, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 783 days.

(21) Appl. No.: 11/122,862

(22) Filed: May 5, 2005

(65) Prior Publication Data

US 2005/0261576 A1 Nov. 24, 2005

(30) Foreign Application Priority Data

May 5, 2004 (DE) ........................ 10 2004 022 061

(51) Int. Cl.
*A61B 5/055* (2006.01)
(52) U.S. Cl. ...................................... 600/420
(58) Field of Classification Search ................. 600/113, 600/114, 428, 410, 413, 419, 420, 431
See application file for complete search history.

(56) References Cited

U.S. PATENT DOCUMENTS

| | | | |
|---|---|---|---|
| 5,419,325 A * | 5/1995 | Dumoulin et al. ........... 600/410 |
| 5,479,925 A | 1/1996 | Dumoulin et al. |
| 5,522,390 A * | 6/1996 | Tuithof et al. ............... 600/410 |
| 5,570,018 A * | 10/1996 | Halse ......................... 324/309 |
| 5,924,987 A * | 7/1999 | Meaney et al. .............. 600/420 |
| 6,728,569 B2 * | 4/2004 | Edelman ..................... 600/410 |
| 2003/0069496 A1 | 4/2003 | Foo |
| 2003/0176782 A1 | 9/2003 | Graessner |
| 2004/0039278 A1 | 2/2004 | Wacker et al. |
| 2004/0068176 A1* | 4/2004 | Kuth .......................... 600/420 |

FOREIGN PATENT DOCUMENTS

EP 0 896 546 11/2002

OTHER PUBLICATIONS

"MR Imaging-Guided Vascular Procedures using CO2 as a Contrast Agent" Wacker et al., American Journal Roentgenological 2003, vol. 81, pp. 485-489.

* cited by examiner

*Primary Examiner*—Eric F Winakur
(74) *Attorney, Agent, or Firm*—Schiff Hardin LLP

(57) ABSTRACT

In a method and apparatus for interventional imaging in magnetic resonance tomography, a contrast agent liquid is prepared by saturation or excitation of the nuclear spins therein, such that it shows with a poor signal in the vessel system of a patient to be examined after injection, or the stationary tissue is prepared by saturation or excitation of the nuclear spins therein such that the contrast agent liquid shows with strong signal (compared to the tissue) in the vessel system of a patient to be examined after injection.

6 Claims, 4 Drawing Sheets

METHOD AND APPARATUS FOR INTERVENTION IMAGING IN MAGNETIC RESONANCE TOMOGRAPHY

BACKGROUND OF THE INVENTION

1. Field of the Invention

The present invention generally concerns magnetic resonance tomography (MRT) as employed in medicine for examination of patients. The present invention in particular concerns a method for improved interventional imaging in MRT using contrast agent liquids.

2. Description of the Prior Art

MRT is based on the physical phenomenon of nuclear magnetic resonance and has been successfully used as an imaging method for over 20 years in medicine and biophysics. In this examination modality, the subject is exposed to a strong, constant magnetic field. The nuclear spins of the atoms in the subject, which were previously randomly oriented, thereby align. Radio-frequency energy can now excite these "ordered" nuclear spins to a specific oscillation. In MRT, this oscillation generates the actual measurement signal that is acquired by appropriate reception coils. By the use of inhomogeneous magnetic fields generated by gradient coils, the measurement subject can be spatially coded in all three spatial directions, which is generally designated as "spatial coding".

The acquisition of the data in MRT ensues in k-space (frequency domain). The MRT image in the image domain is linked with the MRT data in k-space by means of Fourier transformation. The spatial coding of the subject that spans k-space ensues by means of gradients in all three spatial directions. Differentiation is made between the slice selection (establishes an acquisition slice in the subject, typically the x-axis) and the phase coding (determines the second dimensional within the slice, typically the y-axis). Moreover, the selected slice can be subdivided into further slices by phase coding along the z-axis.

A slice is thus initially selectively excited, for example in the z-direction, and a phase coding is possibly implemented in the z-direction. The coding of the spatial information in the slice ensues via a combined phase and frequency coding by means of both of these aforementioned orthogonal gradient fields, which are generated by the likewise aforementioned gradient coils in the x- and y-directions in the example of a slice excited in the z-direction.

In order to acquire data from an entire slice of the subject to be examined, the imaging sequence (for example a gradient echo sequence, FLASH) is repeated N times for different values of the phase coding gradients, for instance $G^y$. The temporal separation of the respectively excited RF pulses is designated as a repetition time TR. The magnetic resonance signal (for example the gradient echo signal) is likewise sampled, digitized, and stored N times in every sequence pass via the $\Delta t$-clocked ADC (analog-digital converter) in equidistant time steps $\Delta t$ in the presence of the read-out gradient $G^x$. In this manner, a number matrix created row-by-row (matrix in k-space, or k-matrix) with N×N data points is obtained. An MR image of the considered slice can be directly reconstructed with a resolution of N×N pixels from this data set via a Fourier transformation (a symmetric matrix with N×N points is only one example, asymmetrical matrices can be generated as well). For physical reasons, the values in the region of the center of the k-matrix primarily contain information about the contrast, the values in the boundary region of the k-matrix predominantly contain information regarding the resolution of the transformed MRT image. Slice images of the human body can be acquired in all directions in the manner just described. MRT as a slice image method in medical diagnostics has primarily excelled as a "non-invasive" examination method. Nevertheless, particularly in angiographic exposures (i.e. exposures of the blood vessels in the human body, especially in organs supplied (perfused) with blood), the contrasting in native MR imaging sets limits that can be significantly expanded by the use of contrast agents. The effectiveness of contrast agents in magnetic resonance tomography is generally based on an influence on the parameters significant to the contrast such as, for example, the longitudinal or transversal relaxation time $T_1$ or $T_2$. Trivalent gadolinium $Gd^{3+}$ that has a $T_1$-reducing effect is prevalent in clinical application. By bonding in complexes known as chelate complexes (DTPA, diethylenetriaminepentaacetic acid), gadolinium loses its toxicity such that Gd-DTPA can normally be applied intravenously. A vein is selected that leads directly to the heart, which ultimately distributes the contrast agent in the entire arterial system. In popular sequences ($T_1$-weighted spin echo sequence, gradient echo sequence, etc.), the accelerated $T_1$ relaxation time effects an increase of the MR signal, thus a brighter representation of the appertaining tissue in the MR image. Sharp and high-contrast images of, for example, head, throat, heart or kidney vessels can be achieved in this manner.

$T_1$ time-reducing contrast agents normally represent low-molecular-weight contrast agents that remain in the vessel only a short time and then diffuse into the interstitial tissue. Alternatively, contrast agents known as "blood pool contrast agents" have been developed that remain in the blood vessels due to their size and that do not diffuse into the interstitial tissue (connective tissue) like low-molecular-weight magnetic resonance contrast agents.

If, in the framework of a vascular intervention, a catheter is introduced into vessels enriched with gadolinium-containing contrast agents, which vessels as such exhibit a high signal intensity, situations frequently occur (for example in the case of an embolization or a stent placement) in which the blood flow distal to the catheter is of great importance and must be monitored. In conventional angiography under x-ray radiography, the flow rates are checked via injection of x-ray contrast agent via the catheter. The vessel system distal to the catheter thereby contrasts and significant information regarding vessel openness, vessel wall condition, flow speed and flow characteristic is acquired. If it is desired to do this monitoring in the same manner under MRT, due to the high signal intensity (explained above) of the contrast agent-enriched blood given use of the typical highly-attenuated, paramagnetic, $T_1$ time-shortening contrast agent such as GadDTPA (Magnevist®), one would attempt to increase the signal intensity. However, it is difficult to make the already-bright blood in the MRT image even brighter. A "contrast agent" ideal for such situations should therefore decrease the signal intensity.

According to the prior art, this ensues, for example, by injection of magnetic liquids that induce susceptibility artifacts and that significantly weaken or obliterate the magnetic resonance signal. The use of unattenuated or slightly attenuated gadolinium-DTPA-containing contrast agents or of iron-oxide contrast agents (for example SPIO, USPIO) is typical.

This method is limited, however, to only a few injection measurements because the recommended highest dose of these substances is very low.

As an alternative, it is possible to inject a proton-poor or proton-free substance that suppresses the blood for a short time. The injection of CO2 is cited as an example for this, which was proposed on the basis of animal tests by Wacker et al (Wacker et al, MR Imaging-Guided Vascular Procedures using $CO_2$ as a contrast agent, AM Journal Roentgenological 2003; 181: 485-489) and which is described in United States Patent Application Publication No. 2004/0039278. $CO_2$ is in fact a suitable contrast agent that has already been used for a long time in interventional radiology; nevertheless, many users (doctors) balk at injecting a gas into blood vessels. A disadvantage is also that this method can be applied only below the diaphragm. The application of $CO_2$ at the heart or at cerebral vessels is forbidden due to the embolism risk that exists. An alternative solution is of great interest, particularly with regard to both of these cited vessel systems that are important for vascular interventions.

An alternative to direct injection of a contrast agent, for example, would be to saturate or to invert the blood signal itself outside of the image plane. Disadvantages of this method are the short $T_1$ time of the blood (approximately 1500 ms, approximately 100 ms after contrast agent administration) as well as the limitation to applications with sufficient blood flow.

SUMMARY OF THE INVENTION

An object of the present invention is to provide a method that further improves the contrast agent-supported interventional imaging in magnetic resonance tomography.

This object is achieved according to the present invention by a method for interventional imaging in magnetic resonance tomography using a contrast agent liquid that is prepared by saturation or excitation, such that it leads to a signal-poor representation after injection into the vessel system of a patient to be examined, or that, by saturation or excitation, the stationary tissue is prepared such that the contrast agent liquid leads to a strong signal representation in the vessel system of a patient to be examined.

The preparation of the stationary tissue can inventively ensue either by emitting one or more saturation pulses or by emitting an inversion pulse into the stationary tissue.

In an embodiment, the contrast agent liquid is provided in a fluid reservoir and the preparation of the contrast agent liquid is implemented by emitting one or more saturation pulses into the fluid reservoir.

The saturation pulse or pulses are advantageously emitted in the form of slice-selective saturation pulses.

In a further embodiment of the inventive method, the contrast agent liquid is provided in a fluid reservoir and the preparation is implemented in the form of an excitation by emitting an inversion pulse into the fluid reservoir.

In a further embodiment of the inventive method, the contrast agent liquid is conducted through a static magnetic gradient field and the preparation is implemented in the form of an excitation by continuous RF irradiation into the flowing contrast agent liquid in the gradient field.

In a version method according to the second and third embodiments, it is advantageous to synchronize the inversion pulse with the point in time of the injection.

The synchronization advantageously ensues such that the contrast agent liquid reaches the zero crossing of the magnetization precisely at the moment when it enters into the vessel to be shown.

The synchronization in accordance with the invention, automatically ensue where necessary via the system computer or the sequence controller.

It is advantageous to apply a phase-sensitive image reconstruction method in the case of an inversion. Given the use of phase-sensitive reconstruction, the contrast can be raised relative to the measurement in the zero crossing of the magnetization if measurement is made before the zero crossing.

In the case of an inversion, it is likewise advantageous to implement the excitation of the contrast agent liquid in an intermediate reservoir that contains precisely the quantity to be applied with an injection.

The injection ensues by hand or mechanically via a pressure injector or infuser.

The invention also encompasses a device that is suitable for implementation of the inventive method.

DESCRIPTION OF THE PREFERRED EMBODIMENTS

Figure 1:
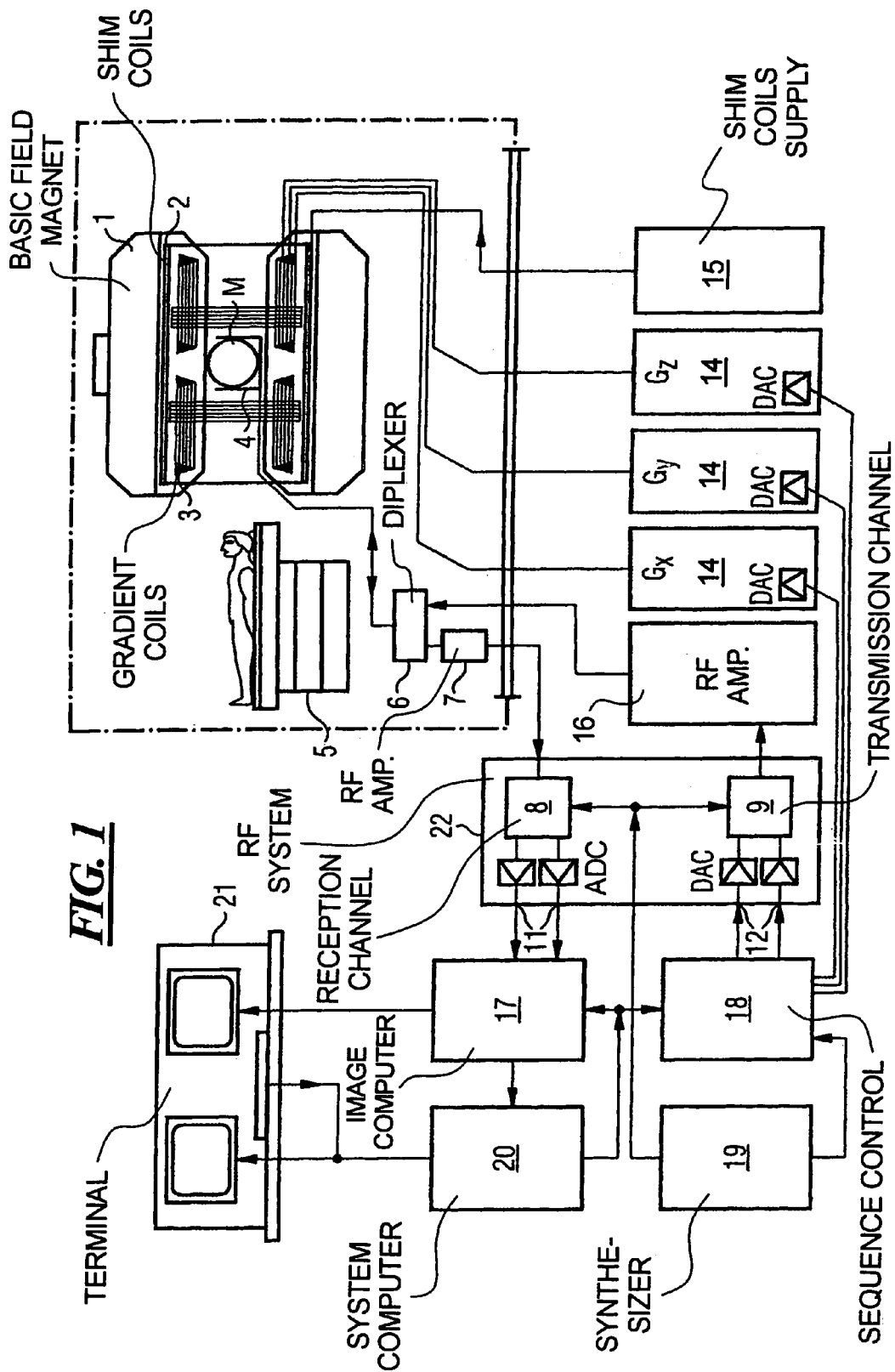
FIG. 1 schematically illustrates a magnetic resonance tomography apparatus operable in accordance with the invention.

FIG. 1 is a block diagram of a magnetic resonance tomography apparatus with which an interventional imaging is possible according to the present invention. The component of the magnetic resonance tomography apparatus correspond to the design of a conventional tomography apparatus with the exceptions described below. A basic field magnet 1 generates a temporally constant strong magnetic field for polarization or alignment of the nuclear spins in the examination region of a subject such as, for example, of a part of a human body to be examined. The high homogeneity of the basic magnetic field necessary for the magnetic resonance scan is defined in a spherical measurement volume M in which the parts of the human body to be examined are introduced. To satisfy the homogeneity requirements, and in particular for elimination of temporally non-varying influences, what are known as shim plates made from ferromagnetic material are mounted at a suitable location. Temporally variable influences are eliminated by shim coils 2 that are activated by a shim current supply 15.

A cylindrical gradient coil system 3 that is composed of three coils is used in the basic field magnet 1. Each coil is supplied with current by an amplifier 14 for generation of a linear gradient field in the respective direction of the Cartesian coordinate system. The first coil of the gradient field system 3 generates a gradient $G_x$ in the x-direction, the second coil generates a gradient $G_y$ in the y-direction and the third coil generates a gradient $G_z$ in the z-direction. Each amplifier 14 has a digital-analog converter that is activated by a sequence controller 18 for time-accurate generation of gradient pulses.

Located within the gradient field system 3 is a radio-frequency antenna 4 that converts the radio-frequency pulses emitted by a radio-frequency power amplifier 16 into a magnetic alternating field for excitation of the nuclei and alignment of the nuclear spins of the subject to be examined or, respectively, of the region of the subject to be examined. The alternating field originating from the precessing nuclear spins (i.e. normally the spin echo signals caused by a pulse sequence composed of one or more radio-frequency pulses and one or more gradient pulses) is also converted by the radio-frequency antenna 4 into a voltage that is supplied via an amplifier 7 into a radio-frequency reception channel 8 of a radio-frequency system 22. The radio-frequency system 22 furthermore has a transmission channel 9 in which are generated the radio-frequency pulses for the excitation of the magnetic nuclear resonance. The respective radio-frequency pulses are digitally represented in the sequence controller 18 as a series of complex numbers according to a pulse sequence predetermined by the system computer 20. This number series is respectively supplied as a real part and an imaginary part via respective inputs 12 to a digital-analog converter in the radio-frequency system 22 and, from this, to the transmission channel 9. In the transmission channel 9, the pulse sequences are modulated with a radio-frequency carrier signal having a base frequency corresponding to the resonance frequency of the nuclear spins in the measurement volume.

The switchover from transmission to reception operation ensues via a transmission-reception diplexer 6. The radio-frequency antenna 4 radiates the radio-frequency pulses into the measurement volume M for excitation of the nuclear spins and samples resulting echo signals. The correspondingly acquired nuclear magnetic resonance signals are phase-sensitively demodulated in the reception channel 8 of the radio-frequency system 22 and translated into a real part and an imaginary part of the measurement signal via respective analog-digital converters. An image is reconstructed by an image computer 17 from the measurement data thus acquired. The administration of the measurement data, the image data and the control programs ensues via a system computer 20. Based on a requirement with control programs, the sequence controller 18 monitors the generation of the respectively desired pulse sequences and the corresponding sampling of k-space. The sequence controller 18 in particular controls the time-accurate switching of the gradients, the emission of the radio-frequency pulses with defined phase and amplitude and the receipt of the nuclear magnetic resonance signals. The time base for the radio frequency system 22 and the sequence controller 18 is provided by a synthesizer 19. The selection of corresponding control programs for generation of a nuclear magnetic resonance image as well as the representation of the generated nuclear magnetic resonance image ensues via a terminal 21 (console) that has a keyboard as well as one or more display screens.

The specified MRT apparatus in accordance with the invention enables the user to prepare a contrast agent liquid in the framework of an interventional imaging and, via a catheter, to introduce higher signal intensity into a vessel system located inside the MRT apparatus, such that the vessel system distal to the catheter contrasts with weak signal or negatively.

As described above, in conventional angiography in magnetic resonance tomography the use of $T_1$-shortening contrast agents leads to a strong signal depiction of the vessel system marked by the contrast agent. In order nevertheless to be able to check flow rates at diverse points under these conditions, contrast agent is introduced via a catheter, the contrast agent being represented with poor signal or a negative signal at the point in time of the exit from the catheter.

The present invention solves this problem by the use of a physiological saline solution or other liquids that exhibit only very slight side effects in comparison to previously used contrast agents, but nevertheless are suitable as contrast agents for magnetic resonance techniques.

For example, physiological saline solution has only the side effects of volume strain for cardiac patients and stress to dialysis patients. Indeed, these patients normally also receive physiological saline solution during an intervention. This could then simply be correspondingly reduced. Nephrotoxic or allergic side effects that frequently occur with presently known contrast agents, and which significantly limit their possibility of usage, do not exist with a physiological saline solution.

Figure 4:
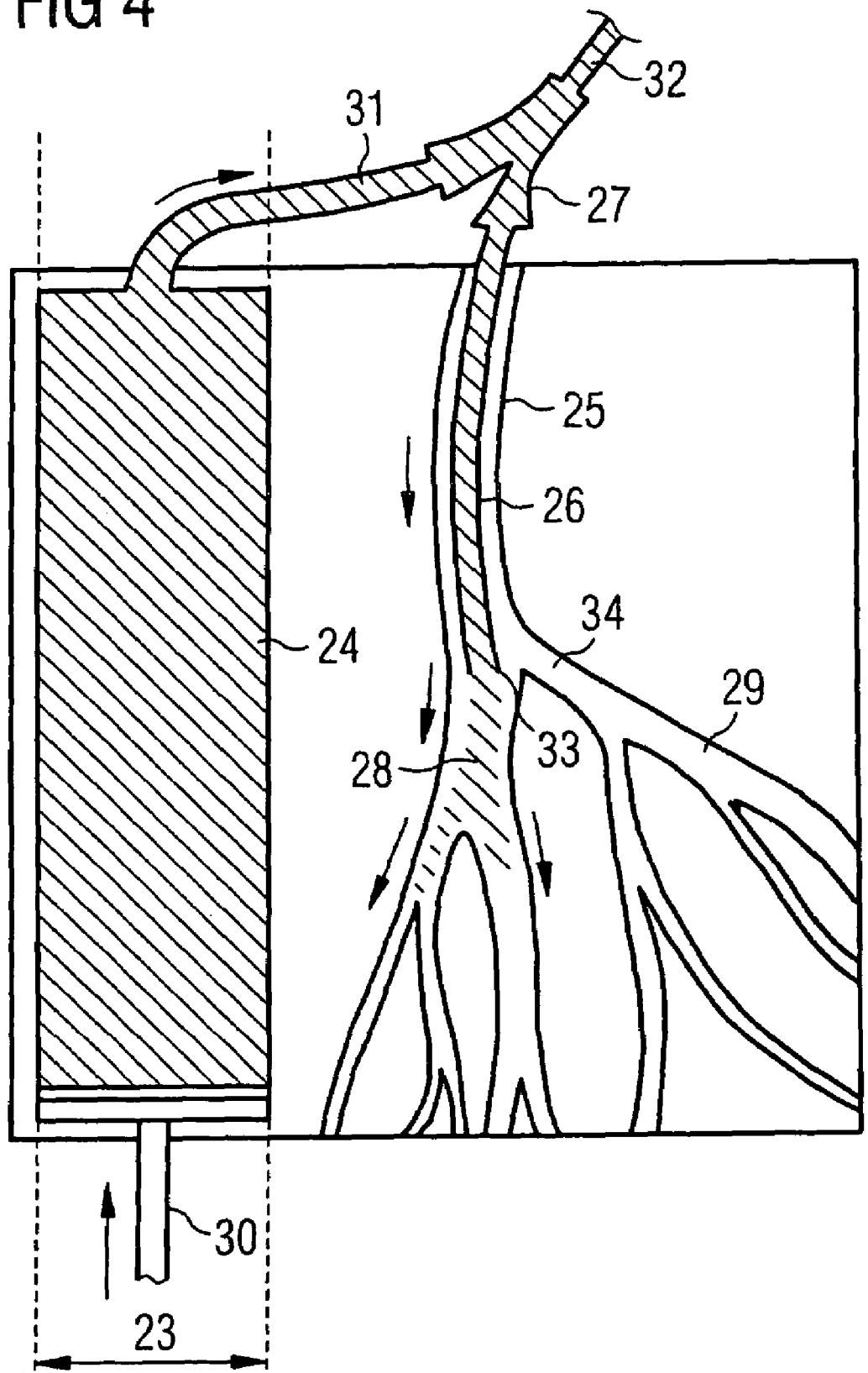
FIG. 4 schematically illustrates the distribution of the signal-decreasing contrast agent in a blood vessel system by means of a catheter originating from a fluid reservoir.

The simplest possibility to make a contrast agent from physiological saline solution is to saturate the spins of the solution by means of a saturation sequence (saturation recovery sequence) and to inject the "saturated solution", still in a saturated state, via a catheter into the signal-poor vessel system to be examined. The technical outlay has proven to be relatively simple, as is explained using FIG. 4:

The physiological saline solution is are sent in a fluid reservoir 24 that is introduced into the field of view next to the patient and remains in the gradient field during the examination. This reservoir 24 is connected with the angiography catheter 26 via a feed line 31 by a y-connector 27. The second leg 32 of the y-connector 27 enables the simultaneous use of a guide wire (not shown) in order to place the catheter tip 33 at the desired position in the vessel system 25 (here bifurcation 34). The fluid reservoir 24 is at a suitable location with a needle for manual injection or with a pressure injector 30 for automatic injection.

After positioning the patient, the fluid reservoir 24 is localized on an overview image (scout image) before the beginning of the intervention. The saturation pulses are subsequently adapted with the aid of a user interface. In the simplest case, in addition to the continuously proceeding image sequence in the framework of the intervention monitoring in the slice region 23 of the fluid reservoir 24, a slice-selective saturation pulse (in the simplest case a 90° RF pulse in combination with slice selection gradient pulse) is used that saturates the liquid in the fluid reservoir 24.

By movement of the injection plunger 30 in the arrow direction, the liquid is injected directly into the catheter 26 via a feed line 31. Due to the relatively long $T_1$ time of pure water (approximately 3 seconds), given a sufficiently fast transit time through feed line 31 and catheter 26 and given a sufficiently high image frame rate, the protons of the liquid are still in a saturated state when they exit from the catheter and cause a signal decrease of the signal-intensive blood in the region 28 distal to the catheter.

Figure 2:
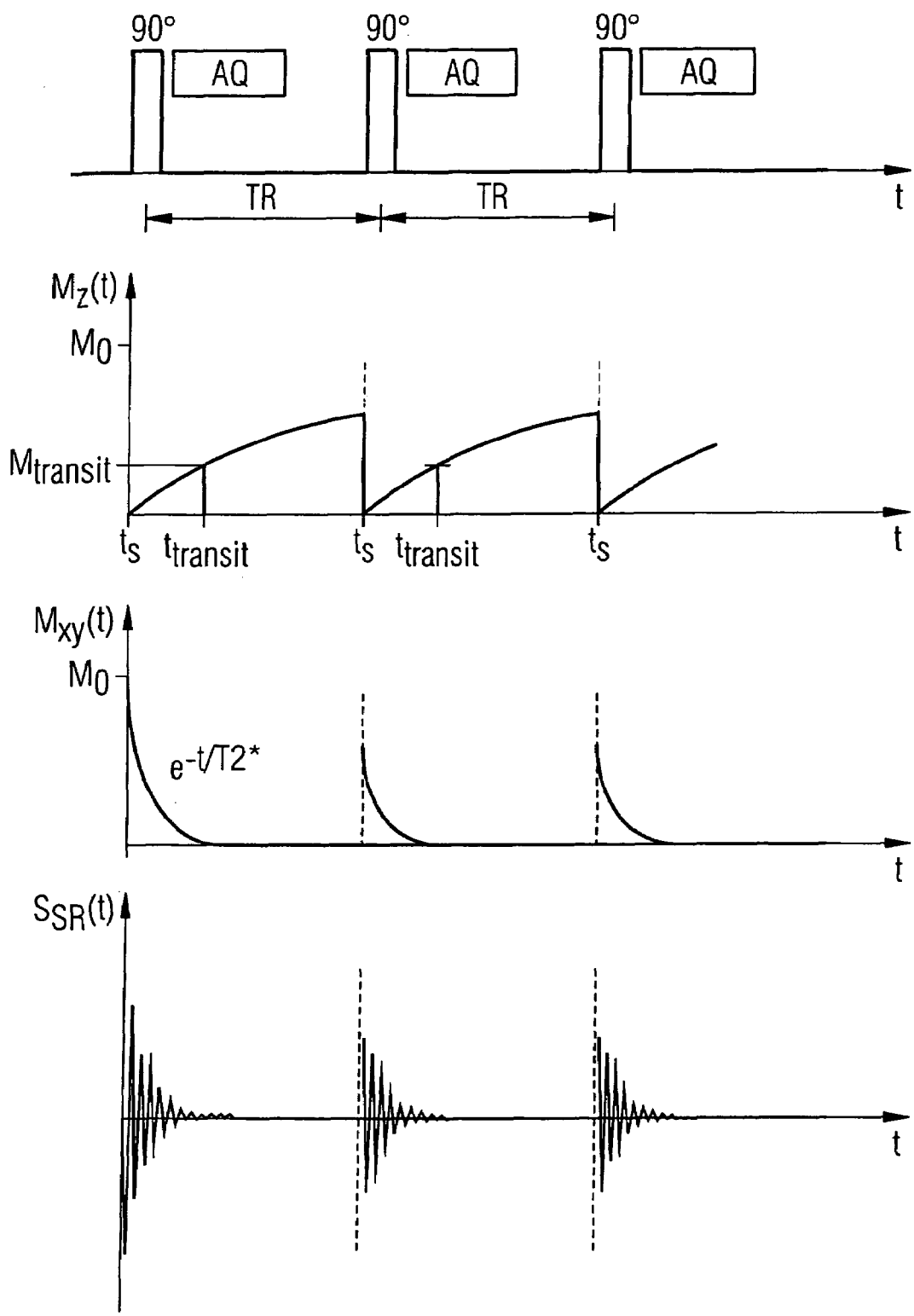
FIG. 2 schematically illustrates the repeated saturation of the longitudinal magnetization via successive 90° RF pulses.

The strength or the degree of the signal decrease of the injected saline solution is, in fact, dependent on the longitudinal relaxation time $T_1$ and therewith dependent on the transit time (flow time through feed line and catheter), as is made clear using FIG. 2.

The pulses of the saturation sequence (SR sequence) used is shown in FIG. 2. The SR sequence includes only a single RF pulse (for example 90° saturation pulse) that achieves the longitudinal magnetization $M_Z$ in the x-y plane, which is generally designated as a saturation since a signal-producing longitudinal magnetization no longer exists at this point in time. After a delay time (the repetition time $T_R$) the sequence is repeated. During this time $T_R$, the spin system regenerates up to a certain degree, i.e. the longitudinal magnetization again approaches the equilibrium magnetization $M_0$. The speed of this process (the curve progress of $M_Z(t)$) is characterized by the longitudinal relaxation time $T_1$. If the repetition time $T_R$ is large in comparison with the $T_1$ time, the magnetization M can completely relax after the excitation and return to the equilibrium magnetization $M_0$. However, in the case of FIG. 2 only the reduced longitudinal magnetization $$M_Z = M_0 \left(1 - e^{\frac{-T_R}{T_1}}\right)$$

rotates in the x-y plane.

A complete saturation, and therewith a complete signal obliteration, is thus produced only exactly at the point in time $t_S$. However, the transport of the saturated material from the fluid reservoir 24 via feed lines to the catheter tip always requires a certain minimum time $t_{transit}$ during which the magnetization always relaxes up to a certain degree ($M_{transit}$), which ultimately always still supplies signal in the field of view or in the reconstructed image. An injection of completely saturated material via a catheter therefore is not possible with the method just described. If a saturation up to a minimum value $M_{transit}$ in the framework of a catheter-based intervention MR measurement is not acceptable, a different preparation method must ensue for the contrast agent (physiological saline solution).

The present invention uses the fact that a total spin saturation likewise occurs in the framework of the inversion method (inversion recovery method, IR method). In the IR method (schematically shown in FIG. 3), the longitudinal magnetization is initially inverted via a 180° pulse (inversion pulse) that is followed by a 90° pulse (readout pulse) after an inversion time $T_1$. The free induction decay $S_{IR}(t)$ (FID signal) is acquired directly after the 90° pulse.

Figure 3:
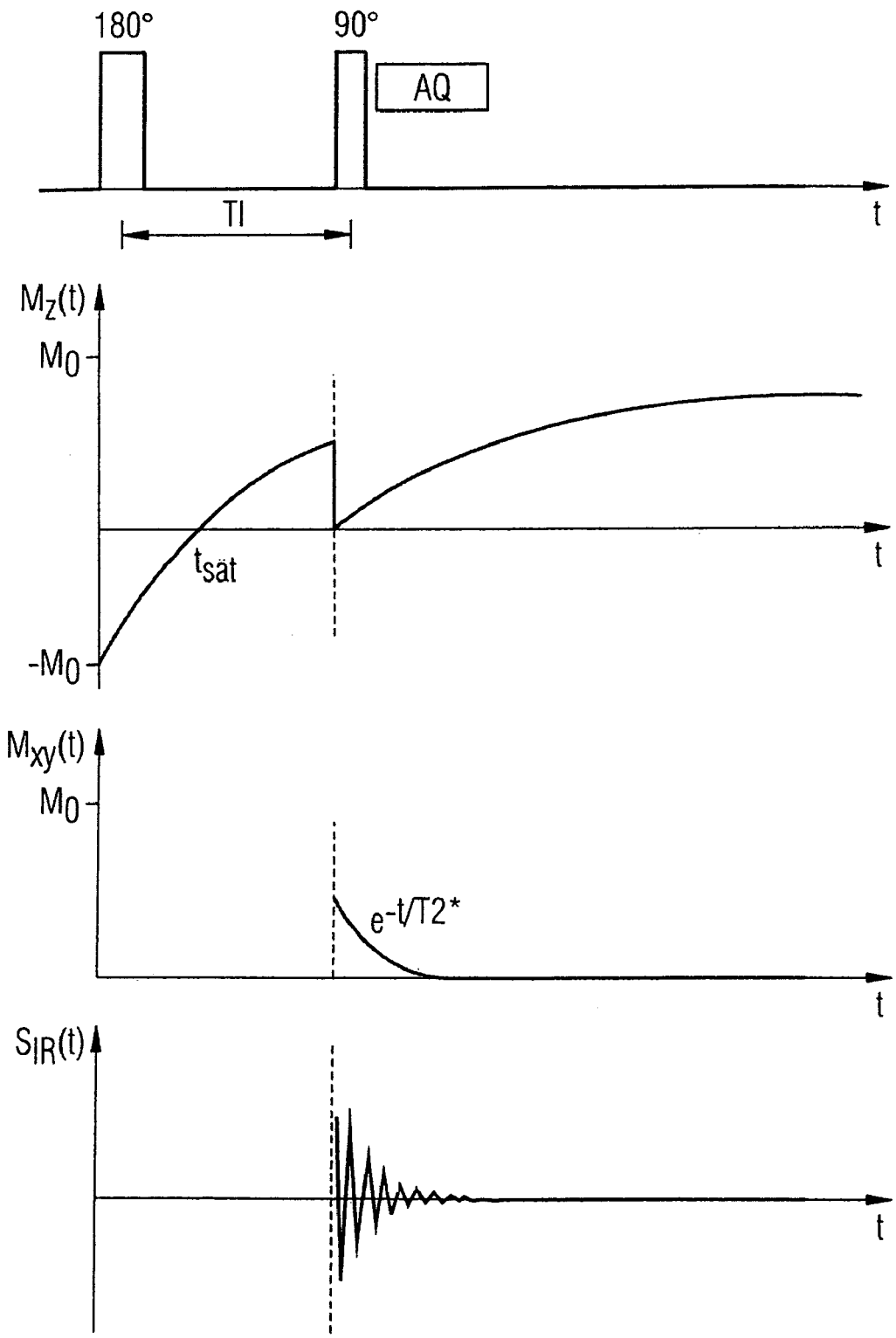
FIG. 3 schematically illustrates the inversion of the longitudinal magnetization via radiation of a 180° RF pulse.

As can be seen in the second diagnosis of FIG. 3, after the initial inversion by the 180° pulse there is a point in time $t_{sat}$ at which the magnetization exhibits a zero crossing. The state of the spins at this zero crossing amounts to a total saturation, since at this point in time ($t_{sat}$) the entire magnetization is equally distributed in the x-y plane.

Instead of a simple saturation (for example via a 90° RF pulse), an inversion of the spins (via a 180° inversion pulse) also leads to a saturation. Due to the time delay between the inversion pulse and the zero crossing, in the framework of a catheter-based intervention MRT imaging it is inventively possible to saturate the liquid exactly at the moment at which it exits from the catheter. The transit time of the inverted liquid must correspond exactly to $t_{sat}$, which inventively ensues by synchronization of the injection with the radiation of the inversion pulses. It must also be ensured that, given such a "pulsed inversion", the inversion pulse is applied only once to the contrast agent, since a further inversion pulse would nullify the saturation process. Both can be achieved, for example, by implementing the inversion in an intermediate reservoir that contains precisely the quantity to be applied with an injection. The inversion pulse is thereby automatically initiated at the beginning of the injection or the injection is mechanically controlled (pressure injector, infuser) by the apparatus or system computer in order to synchronize it with the inversion pulse.

The inversion method can be used when the imaging already ensues before $t_{sat}$. In this case, after the event must be phase-sensitively (speed coded) reconstructed in the image reconstruction:

Every measurement volume is characterized by a vector of a defined length and a defined direction in the complex plane. Given measurements before $t_{sat}$, the polarity sign of the signal of the inverted spins reverses relative to the signal of the non-inverted spins. Signals of non-inverted spins then have, for example, a positive sign, signals of inverted spins have a negative sign. If signed images rather than absolute value images are now supplied as an output, the contrast between inverted and non-inverted spins is thus increased relative to measurements at $t_{sat}$. In practice, a phase correction is applied to generate signed images from the complex spin signal. This image reconstruction is therefore designated as a phase-sensitive reconstruction. In such a case the correction parameters typically are acquired from an image that was measured without inversion pulse but otherwise with identical measurement parameters. In this manner, the (180°) inversion in combination with a phase-sensitive reconstruction maximally allows a doubling of the contrast relative to a (90°) saturation.

The preparation of the liquid—by saturation or inversion— can ensue as described above in the imaging volume of the MRT apparatus (i.e. in a homogenous magnetic field given a deactivated gradient) or can occur outside of the volume. In the first case, saturation is most simply achieved within the imaging volume by irradiation of the reservoir with saturation pulses, as has already been described in connection with FIG. 4. Multiple saturation (FIG. 2) is also unproblematic. In the second case, the preparation occurs in an inhomogeneous, but temporally constant, external field.

A stream of continuously inverted spins also can be generated by adiabatic inversion, by exposing the flowing spins to a continuous RF irradiation (typically coherent and with a constant frequency and strength) in a temporally-constant static field gradient, for example in the scatter field of the magnet or in a field induced by $B_0$ field paramagnetic substances. So as not to interrupt the adiabatic event, the $B_0$ field shifts caused by the temporally variable gradients must be small (compared to the RF field strength) at the site of the inversion. Given inversion in the scatter field of the magnet, the RF frequency necessary for irradiation is far removed from the operating frequency (resonance frequency) of the MRT scanner, so interference due to the continuous RF signal, and image artifacts associated therewith, are prevented.

In contrast to the flow-driven adiabatic inversion, saturation in the scatter field with a local RF field is also possible in principle, but due to the high gradients, high capacities are required in order to saturate a final volume. In order to achieve robust saturation with a defined frequency bandwidth, the RF field must be modulated. Various modulation techniques for saturation are described in the MRT literature; a robust simple technique is, for example, the noise radiation.

In principle, it is also possible to reverse the inventive method described above, by saturating or inverting the spins of the stationary tissue, and subsequently injecting unprepared liquid (NaCl solution) into the blood vessel via the catheter. In this manner, similar to "time-of-flight angiography", "fresh spins" are brought into the vessel system that as such are represented as bright. However, it is disadvantageous that a optimal total saturation does not occur, due to the inhomogeneity of the stationary tissue.

It should be noted that the DSA principle (digital subtraction angiography) can be used before and during the injection of the treated (or, in the case of the reverse, the untreated) liquid, by excluding a mask (created beforehand) is excluded from the background (anatomical tissue) by subtraction given serial acquisition of the same slice.

Although modifications and changes may be suggested by those skilled in the art, it is the intention of the inventors to embody within the patent warranted hereon all changes and

We claim as our invention:

1. A method for interventional imaging of a vessel of interest, surrounded by stationary tissue, in a vessel system, by magnetic resonance tomography, comprising the steps of:
    (a) implementing a preparation selected from the group consisting of:
        (1) preparing a contrast agent liquid in a fluid reservoir by emitting an inversion pulse into the contrast agent liquid in the fluid reservoir that will cause the contrast agent liquid to generate a weak magnetic resonance signal compared to said stationary tissue in a magnetic resonance image of said vessel of interest with said contrast agent liquid therein and said stationary tissue, and
        (2) preparing the stationary tissue by emitting an inversion pulse into said stationary tissue that will cause said stationary tissue to generate a weak magnetic resonance signal compared to said contrast agent liquid in a magnetic resonance image of said vessel of interest with said contrast agent liquid therein and said stationary tissue;
    (b) injecting said contrast agent liquid into said vessel system at an injection point in time;
    (c) synchronizing said inversion pulse relative to said injection point in time by:
        (1) if preparation (a)(1) is selected, emitting said inversion pulse into said contrast agent liquid in said reservoir at a time relative to said injection point in time to give said contrast agent liquid a magnetization that has a zero crossing that occurs when said contrast agent liquid enters into said vessel of interest, and
        (2) if preparation (a)(2) is selected, emitting said inversion pulse into said stationary tissue at a time relative to said injection point in time to give said stationary tissue a magnetization that has a zero crossing that occurs when said contrast agent liquid enters into said vessel of interest; and
    (d) after step (b), acquiring magnetic resonance data from said vessel of interest and said stationary tissue and generating said magnetic resonance image from the acquired magnetic resonance data.

2. A method as claimed in claim 1 wherein step (d) comprises acquiring said magnetic resonance data and phase-sensitively reconstructing said magnetic resonance image of at least a portion of said vessel system using said magnetic resonance data.

3. A method as claimed in claim 1 comprising selecting preparation (a)(1) and providing only a precise amount of said contrast agent liquid that is necessary for injection into said vessel system in said fluid reservoir, and emitting said inversion pulse into said precise amount of said contrast agent liquid in said reservoir.

4. A magnetic resonance tomography apparatus for interventional imaging of a vessel of interest, surrounded by stationary tissue, in a vessel system, comprising:
    a magnetic resonance scanner configured to interact with a subject in whom said vessel system is located;
    a contrast agent injector comprising a fluid reservoir containing contrast agent fluid;
    a control unit that operates said magnetic resonance scanner in a preparation mode selected from the group consisting of:
        a contrast agent liquid preparation mode wherein said scanner emits an inversion pulse into said contrast agent liquid in said fluid reservoir that will cause the contrast agent liquid to generate a weak magnetic resonance signal compared to said stationary tissue in a magnetic resonance image of said vessel of interest with said contrast agent liquid therein and said stationary tissue, and
        a stationary tissue preparation mode wherein said scanner emits an inversion pulse into said stationary tissue that will cause said stationary tissue to generate a weak magnetic resonance signal compared to said contrast agent liquid in a magnetic resonance image of said vessel of interest with said contrast agent liquid therein and said stationary tissue;
    said control unit being configured to operate said contrast agent injector to inject said contrast agent liquid into said vessel system at an injection point of time;
    said control unit being configured to synchronize operation of said scanner to emit said inversion pulse relative to said injection point in time by:
        if said contrast agent liquid preparation mode is selected, causing said scanner to emit said inversion pulse into said contrast agent liquid in said reservoir relative to said injection point in time to give said contrast liquid a magnetization that has a zero crossing that occurs when said contrast agent liquid enters into said vessel of interest, and
        if said stationary tissue preparation mode is selected, operating said scanner to emit said inversion pulse into said stationary tissue at a time relative to said injection point in time to give said stationary tissue a magnetization that has a zero crossing that occurs when said contrast agent liquid enters into said vessel of interest; and
        said control unit being configured to operate said scanner to acquire magnetic resonance data from said subject after injection of said contrast agent and to generate said magnetic resonance image from the acquired magnetic resonance data.

5. An apparatus as claimed in claim 4 wherein said image computer phase-sensitively reconstructs said magnetic resonance image of at least a portion of said vessel system using said magnetic resonance data.

6. An apparatus as claimed in claim 4 wherein said fluid reservoir contains a precise amount of said contrast agent liquid that is necessary for injection into said vessel system, and wherein said scanner is operated in preparation mode (a)(1) to emit said inversion pulse into said precise amount of said contrast agent liquid in said reservoir.

* * * * *